United States Patent
Jang et al.

(10) Patent No.: US 8,152,782 B2
(45) Date of Patent: Apr. 10, 2012

(54) ENDOLUMINAL OCCLUSION-IRRIGATION CATHETER WITH ASPIRATION CAPABILITIES AND METHODS OF USE

(75) Inventors: Yue-Teh Jang, Fremont, CA (US); Ross S. Tsugita, Mountain View, CA (US); Bruce S. Addis, Redwood City, CA (US); Tracy D. Maahs, Santa Clara, CA (US); Jean C. Chang, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/784,264

(22) Filed: May 20, 2010

(65) Prior Publication Data

US 2010/0222736 A1    Sep. 2, 2010

Related U.S. Application Data

(63) Continuation of application No. 11/220,227, filed on Sep. 6, 2005, now Pat. No. 7,731,683, which is a continuation of application No. 09/470,026, filed on Dec. 22, 1999, now abandoned.

(51) Int. Cl.
*A61M 25/00*    (2006.01)
(52) U.S. Cl. .......................... 604/264; 604/35
(58) Field of Classification Search ............ 604/96.01, 604/101.01, 101.04, 102.01, 102.03, 104, 604/103.04, 264, 27, 35, 164.13; 606/191, 606/192, 194
See application file for complete search history.

(56) References Cited

U.S. PATENT DOCUMENTS

| | | | |
|---|---|---|---|
| 3,472,230 A | 10/1969 | Fogarty |
| 3,952,747 A | 4/1976 | Kimmell, Jr. |
| 3,996,938 A | 12/1976 | Clark, III |
| 4,425,908 A | 1/1984 | Simon |
| 4,643,184 A | 2/1987 | Mobin-Uddin |
| 4,662,885 A | 5/1987 | DiPisa, Jr. |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,857,045 A | 8/1989 | Rydell |
| 4,873,978 A | 10/1989 | Ginsburg |
| 4,886,061 A | 12/1989 | Fischell et al. |
| 4,950,238 A | 8/1990 | Sullivan |
| 4,969,891 A | 11/1990 | Gewertz |
| RE33,569 E | 4/1991 | Gifford, III et al. |
| 5,011,488 A | 4/1991 | Ginsburg |
| 5,071,407 A | 12/1991 | Termin et al. |
| 5,116,317 A | 5/1992 | Carson et al. |

(Continued)

FOREIGN PATENT DOCUMENTS

WO    9601591 A1    1/1996

*Primary Examiner* — Bhisma Mehta
(74) *Attorney, Agent, or Firm* — Seager, Tufte & Wickhem LLC

(57) ABSTRACT

A catheter system comprising a guidewire, an endovascular catheter, and an aspiration catheter. The guidewire has an expandable occluder mounted on a distal end. The guidewire and the endovascular catheter are insertable into a lumen of the aspiration catheter. The aspiration catheter also includes infusion and aspiration lumen(s) and port(s). Methods of using the catheter system for treating a vascular lesion and removing embolic material during the procedure are also disclosed.

8 Claims, 10 Drawing Sheets

U.S. PATENT DOCUMENTS

| | | |
|---|---|---|
| 5,133,733 A | 7/1992 | Rasmussen et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,370,657 A | 12/1994 | Irie |
| 5,415,630 A | 5/1995 | Gory et al. |
| 5,419,774 A | 5/1995 | Willard et al. |
| 5,462,529 A | 10/1995 | Simpson et al. |
| 5,536,242 A | 7/1996 | Willard et al. |
| 5,549,626 A | 8/1996 | Miller et al. |
| 5,662,671 A | 9/1997 | Barbut et al. |
| 5,669,933 A | 9/1997 | Simon et al. |
| 5,769,816 A | 6/1998 | Barbut et al. |
| 5,779,716 A | 7/1998 | Cano et al. |
| 5,800,457 A | 9/1998 | Gelbfish |
| 5,800,525 A | 9/1998 | Bachinski et al. |
| 5,807,398 A | 9/1998 | Shaknovich |
| 5,814,064 A | 9/1998 | Daniel et al. |
| 5,833,650 A | 11/1998 | Imran |
| 5,843,022 A | 12/1998 | Willard et al. |
| 5,848,964 A | 12/1998 | Samuels |
| 5,873,889 A | 2/1999 | Chin |
| 5,911,734 A | 6/1999 | Tsugita et al. |
| 5,928,181 A | 7/1999 | Coleman et al. |
| 5,938,645 A | 8/1999 | Gordon |
| 6,013,085 A | 1/2000 | Howard |
| 6,022,336 A | 2/2000 | Zadno-Azizi et al. |
| 6,066,149 A | 5/2000 | Samson et al. |
| 6,066,158 A | 5/2000 | Engelson et al. |
| 6,080,170 A * | 6/2000 | Nash et al. .................... 606/159 |
| 6,126,635 A | 10/2000 | Simpson et al. |
| 6,142,987 A | 11/2000 | Tsugita |
| 6,146,370 A | 11/2000 | Barbut |
| 6,152,946 A | 11/2000 | Broome et al. |
| 6,156,048 A | 12/2000 | Wulfman et al. |
| 6,165,196 A | 12/2000 | Stack et al. |
| 6,168,579 B1 | 1/2001 | Tsugita |
| 6,171,327 B1 | 1/2001 | Daniel et al. |
| 6,179,861 B1 | 1/2001 | Khosravi et al. |
| 6,190,353 B1 | 2/2001 | Makower et al. |
| 6,190,355 B1 | 2/2001 | Hastings |
| 6,190,357 B1 | 2/2001 | Ferrari et al. |
| 6,193,685 B1 | 2/2001 | Goodin |
| 6,203,561 B1 | 3/2001 | Ramee et al. |
| 6,206,868 B1 | 3/2001 | Parodi |
| 6,221,006 B1 | 4/2001 | Dubrul et al. |
| 6,254,571 B1 | 7/2001 | Hart |
| 6,277,139 B1 | 8/2001 | Levinson et al. |
| 6,398,773 B1 | 6/2002 | Bagaoisan et al. |
| 6,423,032 B2 | 7/2002 | Parodi |
| 6,443,922 B1 | 9/2002 | Roberts et al. |
| 6,443,924 B1 | 9/2002 | Rowland et al. |
| 6,451,043 B1 | 9/2002 | McInnes et al. |
| 6,454,741 B1 | 9/2002 | Muni et al. |
| 6,485,500 B1 | 11/2002 | Kokish et al. |
| 6,503,224 B1 | 1/2003 | Forman et al. |
| 6,544,276 B1 | 4/2003 | Azizi |
| 6,558,401 B1 | 5/2003 | Azizi |
| 6,589,214 B2 | 7/2003 | McGuckin, Jr. et al. |
| 6,595,953 B1 | 7/2003 | Coppi et al. |
| 6,605,102 B1 | 8/2003 | Mazzocchi et al. |
| 6,652,546 B1 | 11/2003 | Nash et al. |
| 6,669,662 B1 | 12/2003 | Webler |
| 6,682,505 B2 | 1/2004 | Bates et al. |
| 6,682,543 B2 | 1/2004 | Barbut et al. |
| 6,749,619 B2 | 6/2004 | Ouriel et al. |
| 6,755,813 B2 | 6/2004 | Ouriel et al. |
| 6,805,692 B2 | 10/2004 | Muni et al. |
| 6,849,068 B1 | 2/2005 | Bagaoisan et al. |
| 7,731,683 B2 * | 6/2010 | Jang et al. .................. 604/96.01 |
| 2001/0039411 A1 | 11/2001 | Johansson et al. |
| 2001/0044598 A1 | 11/2001 | Parodi |
| 2001/0047147 A1 | 11/2001 | Slepian et al. |
| 2001/0047184 A1 | 11/2001 | Connors |
| 2001/0049517 A1 | 12/2001 | Zadno-Azizi et al. |
| 2001/0056274 A1 | 12/2001 | Perkins et al. |
| 2002/0016564 A1 | 2/2002 | Courtney et al. |
| 2002/0016565 A1 | 2/2002 | Zadno-Azizi et al. |
| 2002/0065507 A1 | 5/2002 | Zadno-Azizi |
| 2002/0091362 A1 | 7/2002 | Maginot et al. |
| 2002/0091407 A1 | 7/2002 | Zadno-Azizi et al. |
| 2002/0165574 A1 | 11/2002 | Ressemann et al. |
| 2002/0169436 A1 | 11/2002 | Gurm et al. |
| 2002/0183826 A1 | 12/2002 | Dorn et al. |
| 2002/0188276 A1 | 12/2002 | Evans et al. |
| 2003/0009146 A1 | 1/2003 | Muni et al. |
| 2003/0050600 A1 | 3/2003 | Ressemann et al. |
| 2003/0130673 A1 | 7/2003 | Trerotola |
| 2003/0163081 A1 | 8/2003 | Constantz et al. |
| 2004/0006306 A1 | 1/2004 | Evans et al. |
| 2004/0054347 A1 | 3/2004 | Zadno-Azizi et al. |
| 2004/0059372 A1 | 3/2004 | Tsugita |
| 2004/0064179 A1 | 4/2004 | Linder et al. |
| 2004/0098022 A1 | 5/2004 | Barone |
| 2004/0122362 A1 | 6/2004 | Houser et al. |
| 2004/0153094 A1 | 8/2004 | Dunfee et al. |
| 2004/0220521 A1 | 11/2004 | Barbut |
| 2005/0065460 A1 | 3/2005 | Laird |
| 2005/0065469 A1 | 3/2005 | Tal |
| 2005/0085769 A1 | 4/2005 | MacMahon et al. |
| 2005/0124849 A1 | 6/2005 | Barbut et al. |
| 2005/0131446 A1 | 6/2005 | Coughlin et al. |
| 2005/0131453 A1 | 6/2005 | Parodi |
| 2005/0148997 A1 | 7/2005 | Valley et al. |
| 2005/0149103 A1 | 7/2005 | Connors, III |
| 2005/0154344 A1 | 7/2005 | Chang et al. |
| 2005/0159640 A1 | 7/2005 | Barbut et al. |
| 2005/0228432 A1 | 10/2005 | Hogendijk et al. |
| 2005/0245866 A1 | 11/2005 | Zadno-Azizi |
| 2005/0245894 A1 | 11/2005 | Zadno-Azizi |

* cited by examiner

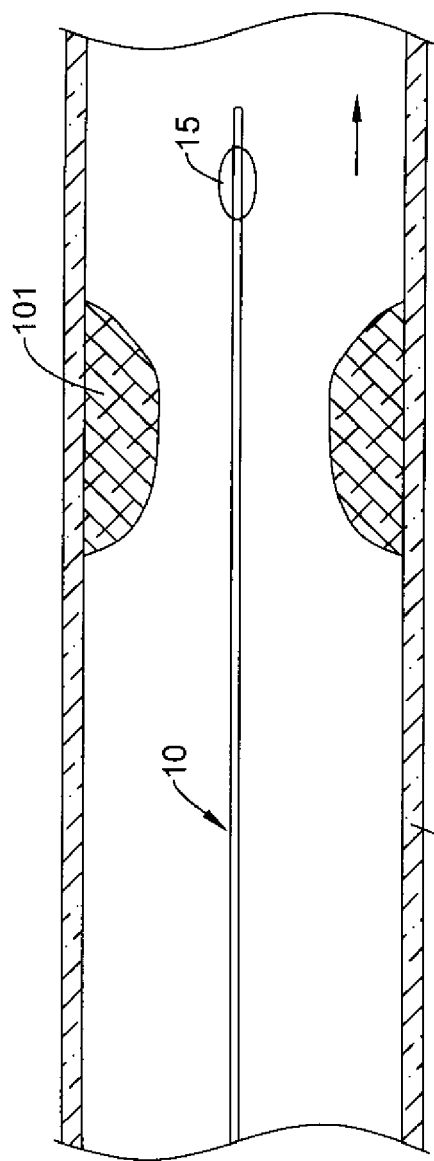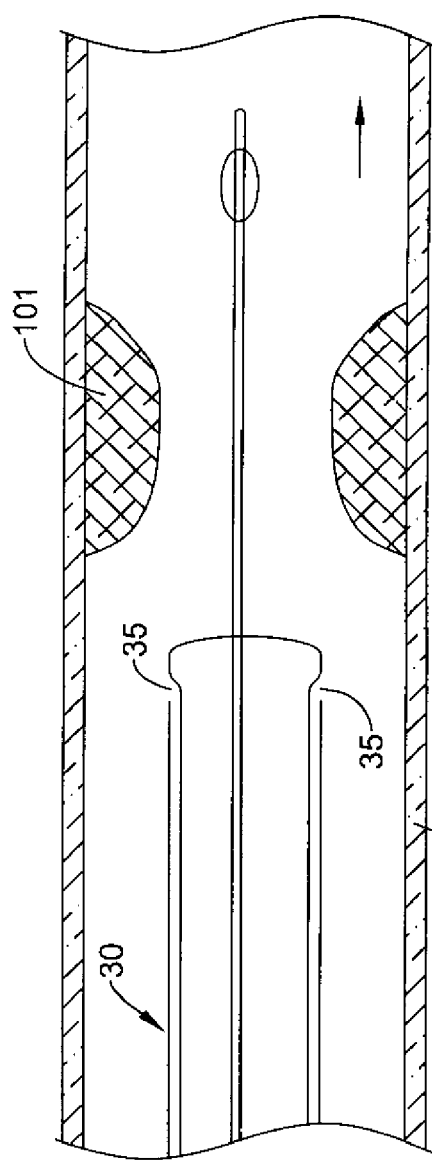

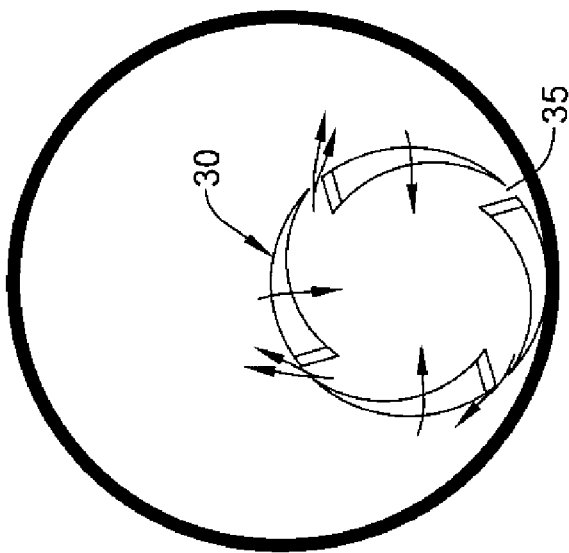
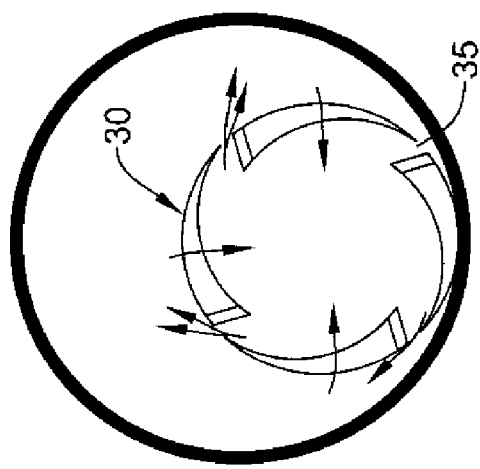
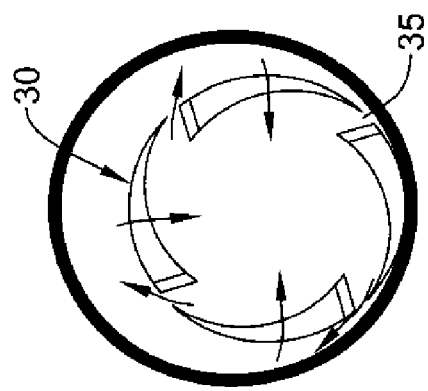
Figure 7

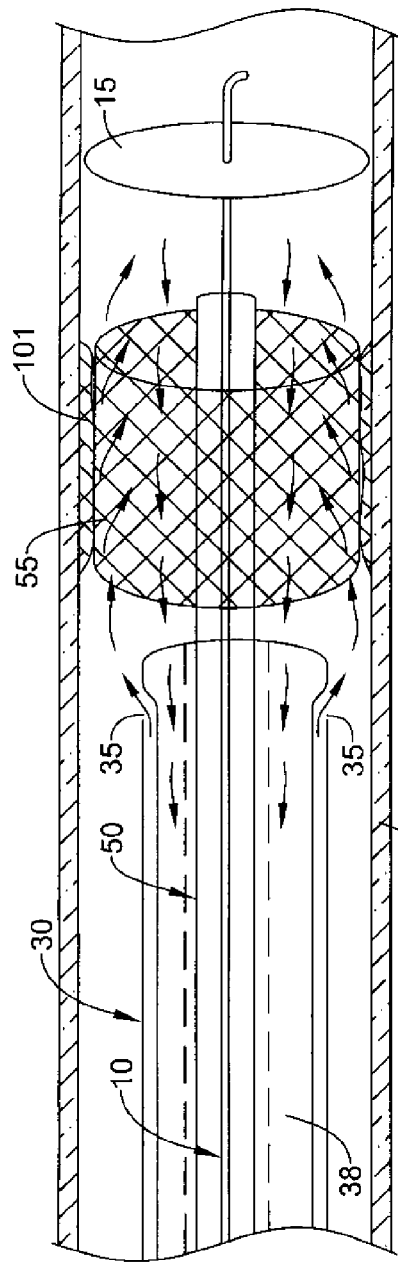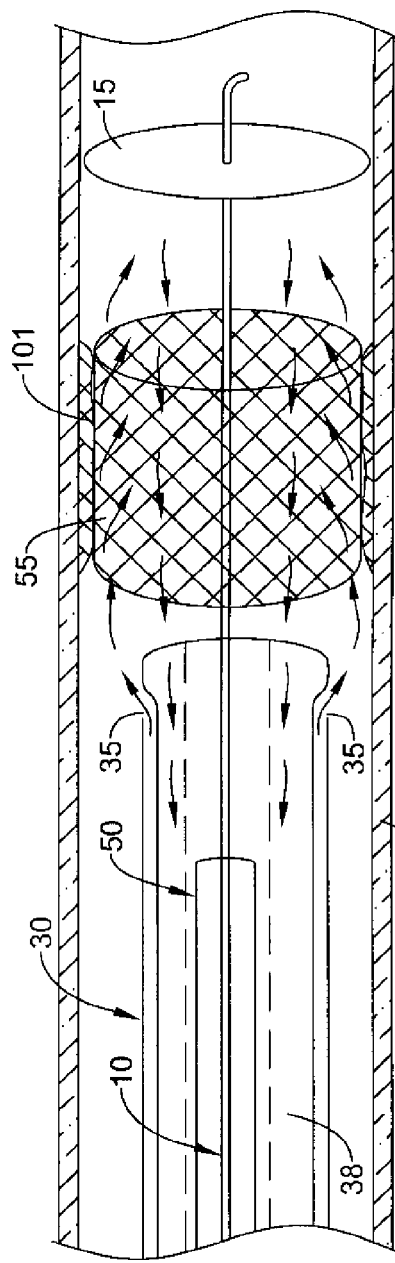
Figure 9A
Figure 9B

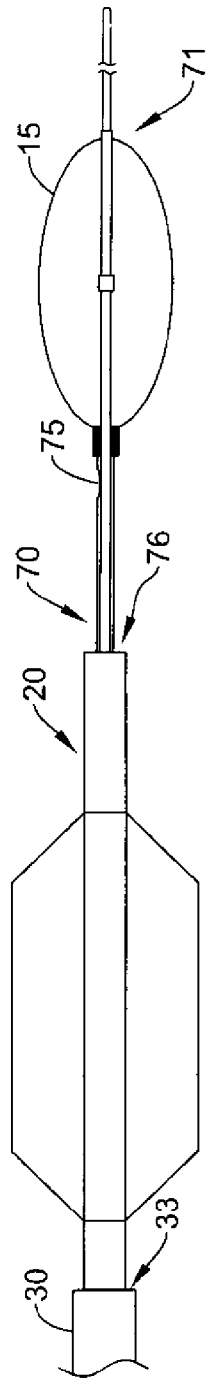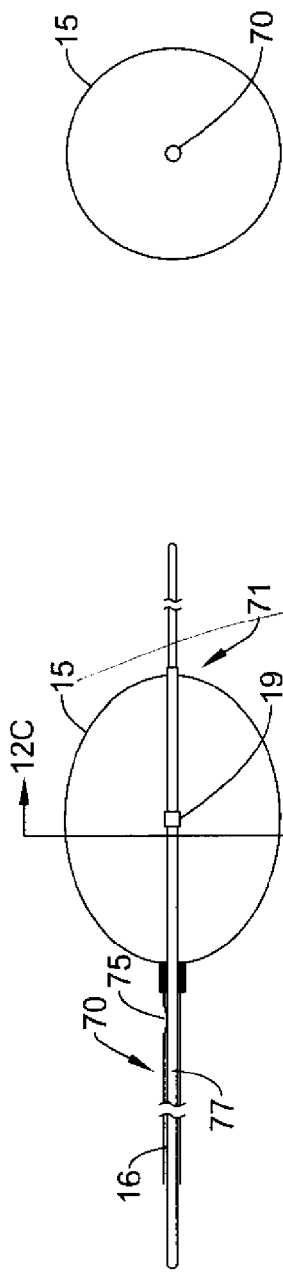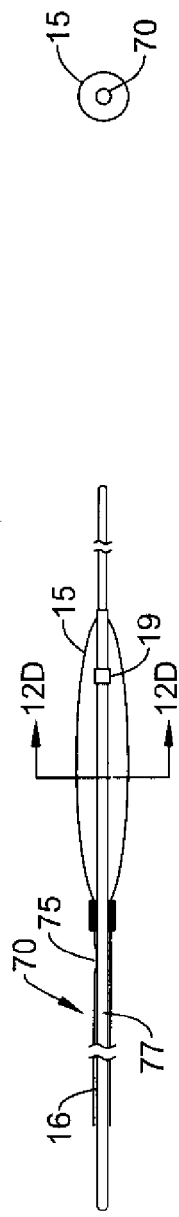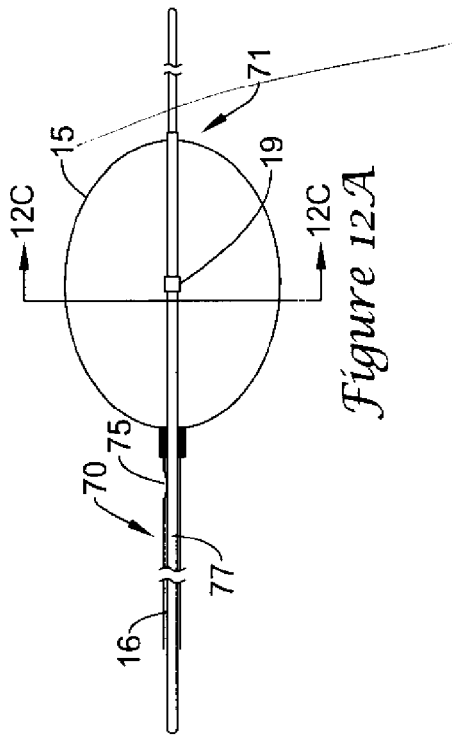

ENDOLUMINAL OCCLUSION-IRRIGATION CATHETER WITH ASPIRATION CAPABILITIES AND METHODS OF USE

This is a continuation application of U.S. application Ser. No. 11/220,227 filed Sep. 6, 2005, now U.S. Pat. No. 7,731, 683, which is a continuation of U.S. application Ser. No. 09/470,026,filed Dec. 22, 1999, now abandoned.

FIELD OF THE INVENTION

The present invention generally relates to medical devices for protecting a patient from distal embolization during interventional procedures, such as angioplasty or stent placement for treatment of vascular stenosis. More particularly, the devices comprise a catheter having irrigation and aspiration capabilities, and a guidewire carrying a distal expandable occluder. An endovascular instrument, such as an angioplasty catheter, is insertable into a lumen of the aspiration catheter.

BACKGROUND OF THE INVENTION

Treatments of vascular stenosis or lesions during endovascular procedures, such as atherectomy, balloon angioplasty with or without stent placement, or ablation therapy, are associated with increased risk of distal embolization. Tissue debris, calcium, atheromatous plaque, and/or thrombi generated during the procedure often become lodged downstream in a small vessel of vital organs, causing tissue ischemia or infarction. For example, transient ischemic attack (TIA) and cerebral infarction (stroke) are common complications of performing endovascular procedures on the ascending aorta and the carotid artery.

To reduce the risk of distal embolism, several devices are employed for use in endovascular procedures. For example, blood filters can be deployed distal to a vascular lesion to capture emboli. However, disadvantages associated with the blood filters are that (1) dislodgment of embolic material can occur during insertion and retrieval of the filter device, and (2) blood filters cannot easily be used in small vessels, (e.g., a saphenous vein graft measuring 3 or 4 mm).

Another catheter system described in U.S. Pat. No. 5,833, 650 includes occlusion members for providing proximal and distal occlusion to a vascular lesion. Each occlusion member communicates with an inflation lumen. The catheter includes irrigation and aspiration lumens for removing embolic debris generated during the procedure. The catheter also includes a device introducing lumen, which further increases the overall size and diameter of the catheter, making the catheter impracticable for use in smaller vessels.

Theron developed a device having an insertion catheter, a dilation catheter, and an occlusion catheter assembled in a coaxial arrangement, U.S. Pat. No. 5,423,742. The catheter device is inserted across a vascular lesion which is dilated by the dilation catheter. Emboli generated during the dilation is removed by suction through the insertion catheter, while the occlusion catheter provides vascular occlusion distal to the vascular lesion. The major disadvantage associated with the device is that some of the embolic material will not be removed by irrigation and suction, thereby leaving the patient at risk for embolic complication.

Thus, there is a need for devices and methods which effectively remove embolic material generated during endovascular procedures, and that can be used in vessels having various diameters.

SUMMARY OF THE INVENTION

The present invention provides an endoluminal catheter system adapted for insertion into arteries of various sizes, including the femoral artery, the iliac artery, the popliteal artery, the renal artery, the inferior mesenteric artery, the superior mesenteric artery, the celiac artery, the coronary artery, the common carotid artery, the internal carotid artery, the external carotid artery, the subclavian artery, the axillary artery, and the brachial artery. The catheter system is also adapted for insertion into a patient's venous vasculature, including the femoral vein, the iliac vein, the superficial femoral vein, the deep femoral vein, the renal vein, the coronary artery, the internal jugular vein, the external jugular vein, the subclavian vein, the saphenous vein, the azygous vein, the superior vena cava, and the inferior vena cava. The catheter system can accommodate a variety of endovascular instruments, including a blood filter, an angioplasty catheter, a valveoplasty catheter, an electrode catheter, internal vessel segregating or isolating dams, an endoscopic camera, a pressure monitor, a stent, a graft, a shunt, a perfusion catheter, and endoscopic devices.

In a first embodiment, the catheter system includes a guidewire, an endovascular catheter, e.g., angioplasty catheter, and an aspiration catheter. The guidewire has a proximal end, and an expandable occluder mounted on a distal end. The aspiration catheter has first and second lumens. The first lumen communicates between a proximal end and a distal end, and is adapted to receive the guidewire and the endovascular catheter. The second lumen communicates with at least one distal fluid infusion port. In certain embodiments, the catheter includes an aspiration lumen communicating with one or a plurality of distal aspiration ports.

In another embodiment, 2, 3, 4, 5, 6, or any other number of infusion ports are disposed radially about the distal end of the aspiration catheter. The infusion ports are shaped to direct fluid in a circular path radially and distally beyond the distal end of the aspiration catheter. In certain embodiments, the infusion ports are directed radially outward and angled relative to the radius of the catheter.

In another embodiment, the expandable occluder is mounted on a distal end of a support wire, which includes an infusion lumen and port(s). The support wire is insertable through the lumen of the endovascular catheter which includes distal aspiration port(s) and lumen.

In a first method of treating an endovascular lesion using the catheter system described above, the guidewire, which has the expandable occluder placed in a collapsed state, is inserted in the lumen of the aspiration catheter. The aspiration catheter carrying the guidewire is then inserted into a vessel, and the guidewire is advanced to position the occluder distal to a region of interest. An endovascular device, e.g., an angioplasty catheter, is inserted over the proximal end of the guidewire, and advanced to position a dilatation member within the region of interest. The aspiration catheter is advanced over the guidewire and positioned proximal the dilatation member. The occluder on the guidewire is expanded to occlude the vascular lumen distal to the lesion. The dilatation member is expanded to treat the vascular lesion and collapsed after luminal patency is achieved. Fluid, such as saline or Ringer's lactate solution, is infused through the infusion lumen and ports to irrigate the treated lumen. Fluid, blood, and embolic debris are removed through the aspiration lumen under suction. The occluder on the guidewire remains expanded during irrigation and aspiration. In certain embodiments, infusion and aspiration of fluid can create a venturi effect in the vascular lumen between the expanded occluder and the aspiration catheter to facilitate removal of loose emboli and embolic material partially attached to the vascular wall. The surgeon can tell that removal of embolic material is complete after the aspirated fluid turns from red to clear and is free of any debris. In this way, the catheter system is capable of complete removal of emboli.

In another method, fluid is infused through the lumen of a support wire to irrigate the region of interest. Embolic debris, blood, and fluid are removed through the distal aspiration ports and lumen of the endovascular catheter. Radiopaque contrast agent is infused through the infusion lumen to assess luminal patency under fluoroscopy. After treatment of the vascular lesion, the occluder is collapsed, and the catheter system is removed from the vessel.

It will be understood that there are several advantages in using the catheter systems and methods disclosed herein for treating a vascular lesion. For example, the devices (1) can be inserted in arteries or veins of various diameter, (2) provide near-total capture of embolic material, thereby dramatically reducing the risk of distal embolization, (3) accommodate a variety of endovascular instruments, and (4) provide treatment of vascular lesions and emboli protection utilizing one catheter system, thereby obviating the need for device exchange.

BRIEF DESCRIPTION OF THE DRAWINGS

FIG. 2 depicts a guidewire inserted in a vessel.

FIG. 3 depicts an aspiration catheter inserted over the guidewire of FIG. 2.

FIG. 7 depicts cross-sectional views of another embodiment of the aspiration catheter irrigating vascular lumens of varying diameters.

FIG. 9A depicts the catheter system of FIG. 8 deploying a stent into a vessel.

FIG. 9B depicts the stent deployment catheter of FIG. 9A withdrawn into the lumen of the aspiration catheter.

FIG. 11 depicts another embodiment of the catheter system having a support wire inserted through an endovascular catheter.

FIG. 12A depicts an embodiment of the support wire having an expandable occluder mounted on a distal end.

FIG. 12B depicts the occluder of the support wire of FIG. 12A in a collapsed state.

FIG. 12C depicts a cross-sectional view of the support wire of FIG. 12A through section line B-B.

FIG. 12D depicts a cross-sectional view of the support wire of FIG. 12B through section line D-D.

DETAILED DESCRIPTION

Figure 1:
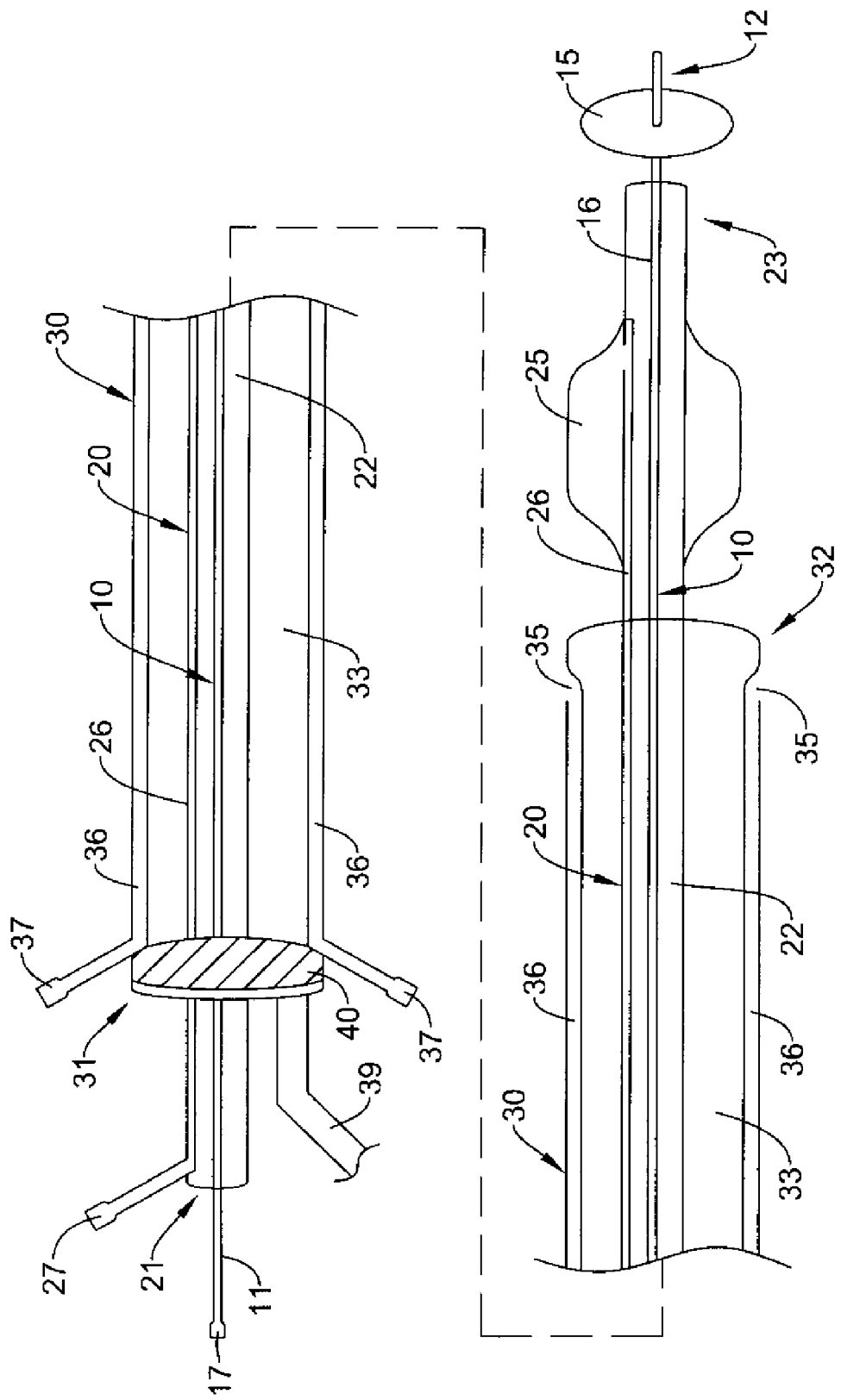
FIG. 1 depicts an embodiment of the catheter system for treating a vascular lesion according to the present invention.

Referring now to the drawings, an embodiment of the catheter system for treating a vascular lesion is depicted in FIG. 1. The system generally comprises guidewire 10, angioplasty catheter 20, and aspiration catheter 30. Guidewire 10 has proximal end 11 and distal end 12. An expandable occluder, shown as balloon 15 which communicates with inflation lumen 16 and proximal port 17, is mounted on distal end 12. Balloon 15 can be expanded by infusing air, gas, or saline through proximal port 17. Guidewire 10 is inserted through lumen 22 of angioplasty catheter 20. Lumen 22 communicates with proximal end 21 and distal end 23. Dilatation member, shown as expandable balloon 25 which communicates with inflation lumen 26 and inflation port 27, is mounted on distal end 23 of the catheter. Dilatation balloon 25 can be expanded by infusing air, gas, or saline through proximal port 27. Angioplasty catheter 20 is inserted through lumen 33 of aspiration catheter 30. Lumen 33 communicates with proximal end 31 and distal end 32. Hemostatic valve 40 is included in proximal end 31 to prevent back flow of blood during catheter insertion. The aspiration catheter includes infusion ports 35 at distal end 32. Each infusion port communicates with infusion lumen 36 and proximal infusion port 37. In certain embodiments, the infusion ports communicate with a single infusion lumen and port. Lumen 33, which communicates with aspiration lumen 39, is adapted for aspiration of fluid, air or debris. Lumen 39 extends from proximal end 31 and is adapted for attachment to a vacuum at a proximal end.

In use, guidewire 10 with balloon occluder 15 in a collapsed state is inserted through an incision on a peripheral artery and advanced to vascular lesion 101 as depicted in FIG. 2. Aspiration catheter 30 is then inserted over guidewire 10 into vessel 100 proximal to lesion 101 as depicted in FIG. 3. Alternatively, guidewire 10 is inserted into lumen 33 of aspiration catheter 30 prior to insertion into the vessel.

Figure 4A:
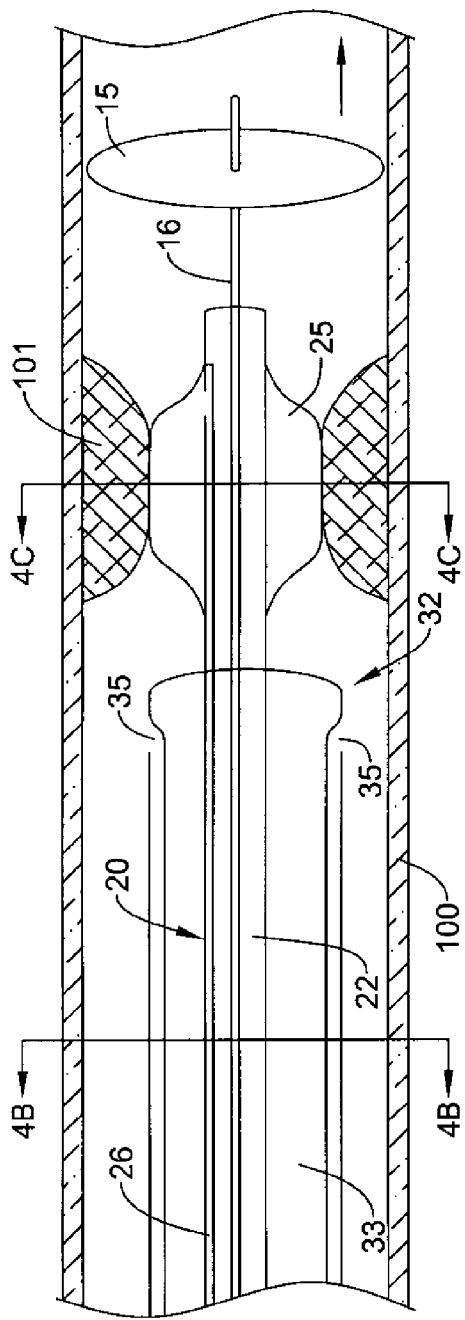
FIG. 4A depicts the catheter system of FIG. 1 inserted in a vessel for treatment of atheromatous lesions.
Figure 4C:
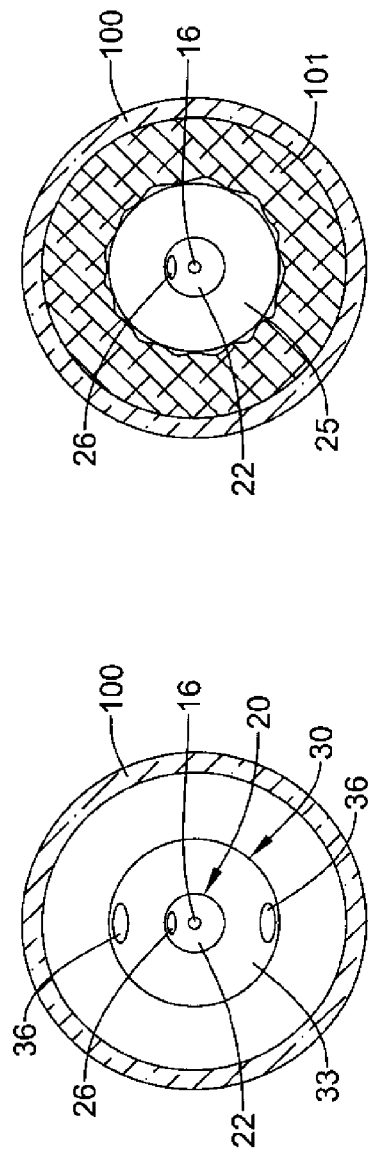
FIG. 4C depicts a cross-sectional view of the catheter system of FIG. 4A through sectional line C-C.
Figure 4B:
FIG. 4B depicts a cross-sectional view of the catheter system of FIG. 4A through sectional line B-B.

Angioplasty catheter 20 is inserted into lumen 33 of aspiration catheter 30 and advanced to position dilatation balloon 25 over lesion 101 as depicted in FIG. 4A. Distal end 32 of the aspiration catheter is positioned proximal of balloon 25. Balloon 15 of the guidewire is then inflated to occlude the lumen of vessel 100, thereby protecting emboli from traveling downstream to other organs when dilatation balloon 25 is expanded against lesion 101. In other methods, balloon 15 is inflated before the positioning of angioplasty catheter 20 in the region of interest, and in other methods before positioning the aspiration catheter 30 proximal to the region of interest. A cross-sectional view of the catheter system proximal to lesion 101 is depicted in FIG. 4B. As shown in FIG. 4B, the aspiration lumen 33 and the infusion lumen 36 may be non-coaxial. A cross-sectional view of the catheter system acting to cause dilation of lesion 101 is depicted in FIG. 4C.

Figure 5A:
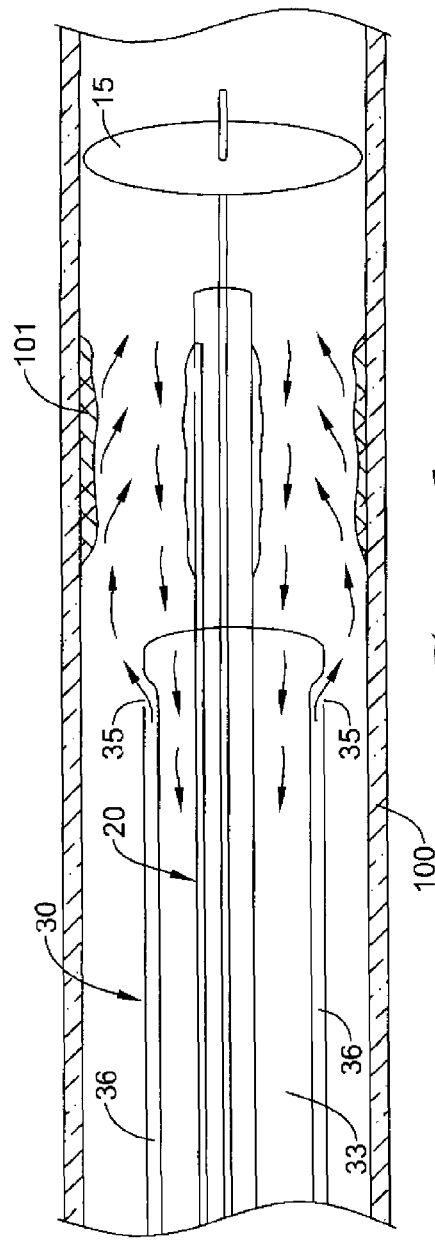
FIG. 5A depicts irrigation and aspiration of vascular debris after angioplasty using the catheter system of FIG. 1.

During angioplasty, inflation of the dilatation balloon often causes fissure of an atheromatous lesion, which commonly includes calcium, cholesterol plaque, and thrombi, thereby liberating embolic debris. After the dilatation balloon is expanded against the atheromatous lesion to re-establish lumenal patency, the dilatation balloon is deflated. Radiopaque contrast agent can be infused through infusion ports 35 to assess the diameter of the vascular lumen under fluoroscopy. Fluid, such as saline or Ringer's lactate solution, is infused through infusion lumens 36 and ports 35 to irrigate the vascular region including the distal end of the angioplasty catheter as shown in FIG. 5A. Lumen 33 is attached to suction, and fluid, blood, and debris are aspirated into lumen 33 and removed. The distal end of the angioplasty catheter is maintained proximal to balloon occluder 15 and distal to aspiration catheter during irrigation and aspiration of embolic debris.

Figure 5B:
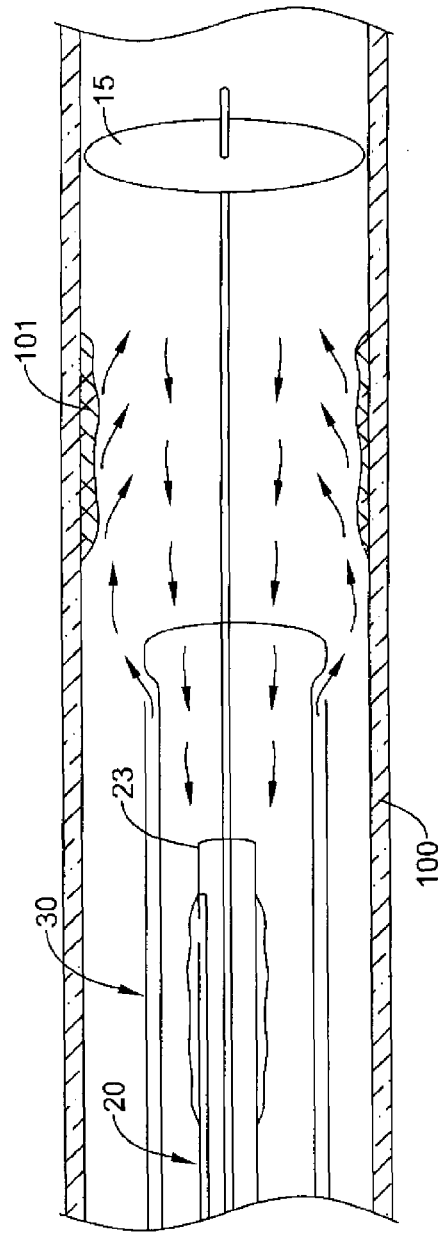
FIG. 5B depicts the catheter system of FIG. 5A having the angioplasty catheter withdrawn within the lumen of the aspiration catheter.

Alternatively, the distal end of angioplasty catheter 20 is withdrawn proximal, into lumen 33 of aspiration catheter 30, in certain cases, prior to irrigation and aspiration as shown in FIG. 5B. The color of the aspirate is monitored at the proximal end of aspiration catheter. Removal of embolic debris is complete when the color of the aspirate turns from red to clear and the aspirate is free of any debris. After angioplasty, balloon 15 on the guidewire is deflated to re-establish vascular flow, and the catheter system is removed from the vessel.

Figure 6A:
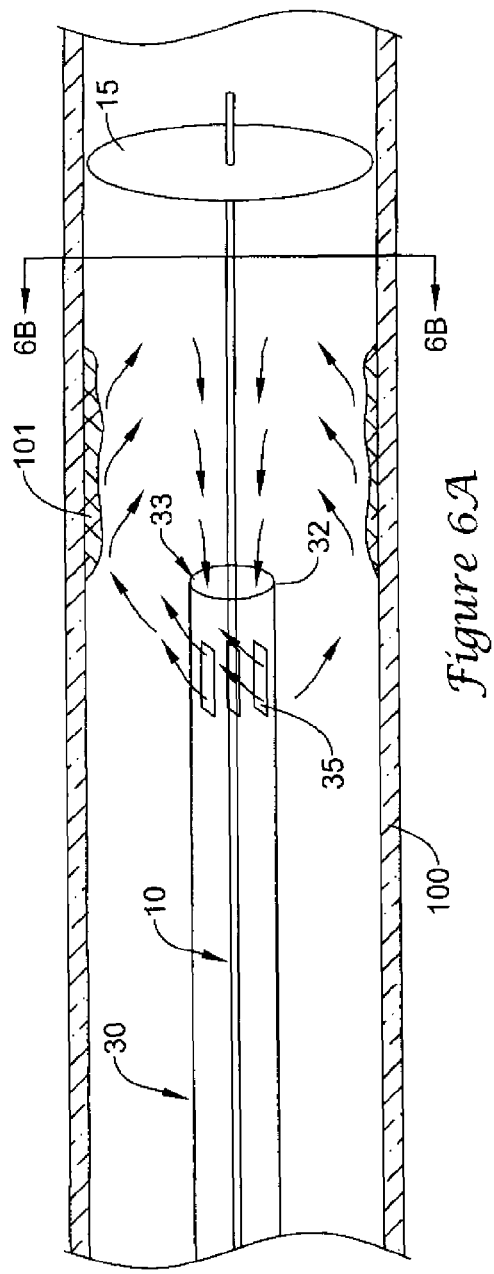
FIG. 6A depicts another embodiment of the aspiration catheter having a plurality of infusion ports shaped to direct fluid flow.
Figure 6B:
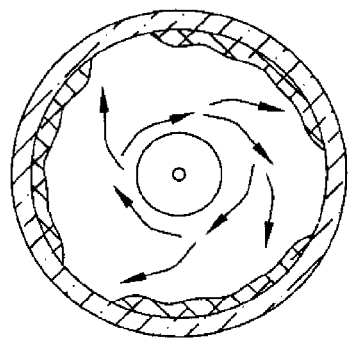
FIG. 6B depicts a distal view of the catheter system of FIG. 6A from cross-sectional line B-B.

FIG. 6A depicts another embodiment of aspiration catheter 30 having a plurality of infusion ports 35 which comprise angled slots. Ports 35 are shaped to direct fluid radially and distally beyond distal end 32. When suction is attached to the lumen of aspiration catheter 30, a venturi effect is created, causing the irrigated fluid to circulate circumferentially about catheter 30, similar to a whirlwind as depicted in FIG. 6B. This irrigation/aspiration system increases the contact of fluid with the vascular wall, thereby increasing the effectiveness of removing embolic debris and loosely attached plaque or thrombi.

FIG. 7 depicts cross-sectional views of another embodiment of aspiration catheter 30 having angled infusion ports 35 for directing fluid flow. Catheter 30 is inserted in vessels of varying diameter. The catheter is also effective in generating a whirlpool-like irrigation pattern when the catheter is positioned adjacent the vascular wall. The catheter can be repositioned within around the vascular lumen to remove embolic debris.

Figure 8:
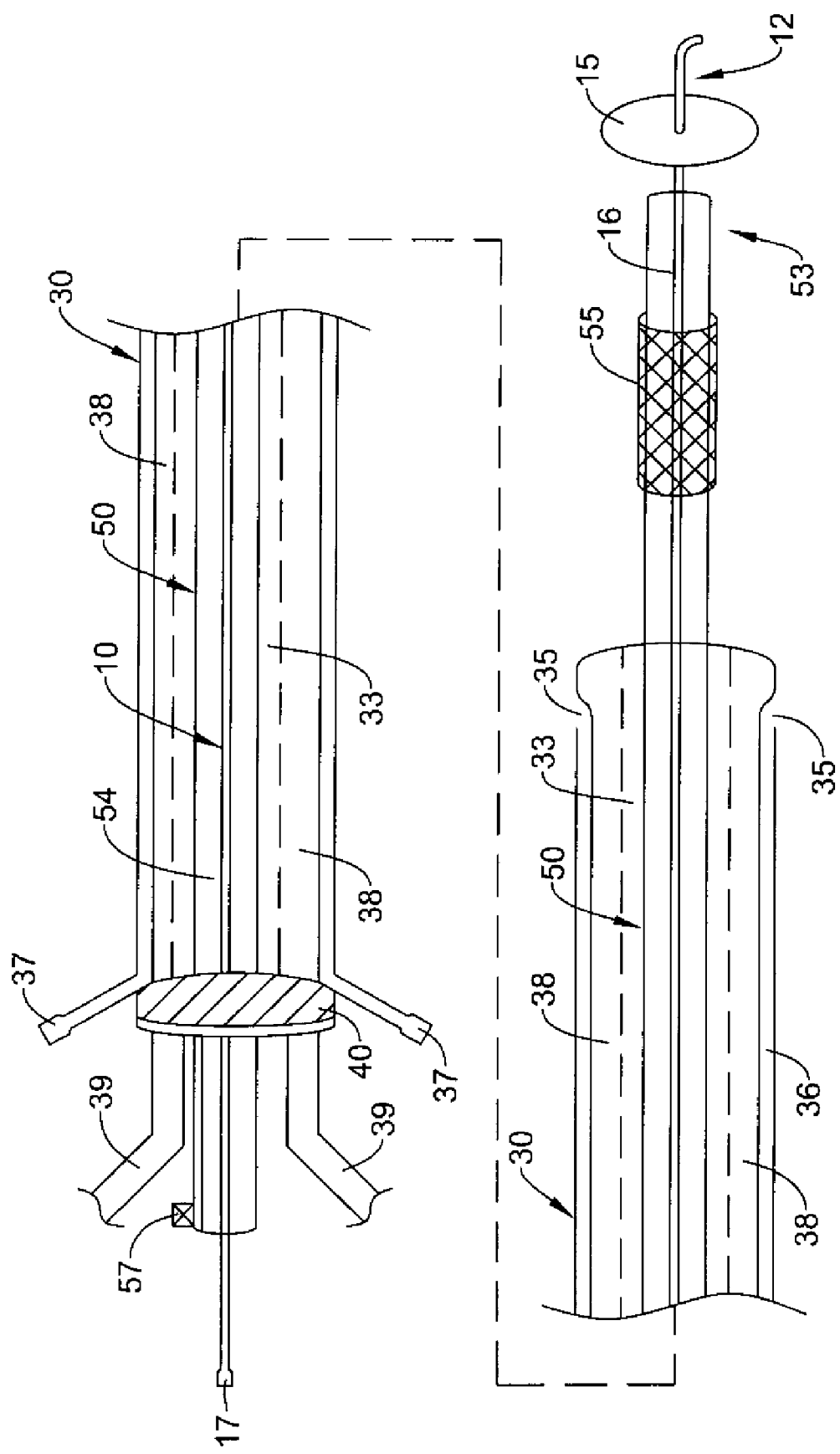
FIG. 8 depicts another embodiment of the catheter system having a stent deployment catheter.

FIG. 8 depicts another embodiment of the catheter system having stent deployment catheter 50 inserted through lumen 33 of aspiration catheter 30. Stent 55 is mounted on distal end 53 of catheter 50 and is operable through actuating mechanism 57 at the proximal end. In certain embodiments, stent 55 is made from shape-memory material, e.g., nitinol. The stent is therefore self-expanding at body temperature and is simply released to actuate. Lumen 54 of catheter 50 is adapted to receive guidewire 10, which has an arcuate distal end 12 to assist guidance through vessels. The aspiration catheter includes infusion ports 35 at distal end 32. Each infusion port communicates with infusion lumen 36 and proximal infusion port 37. Aspiration catheter 30 also includes suction lumens 38, which communicate with aspiration lumens 39 adapted for attachment to a vacuum at a proximal end. In certain embodiments, suction lumens 38 communicate with a single aspiration lumen 39.

In use, aspiration catheter 30 and guidewire 10 with balloon occluder 15 in a collapsed state are inserted into a vessel. The guidewire is advanced distal to vascular lesion 101 as depicted in FIG. 9A. Distal end 32 of the aspiration catheter is positioned proximal lesion 101. Stent deployment catheter 50 with stent 55 in a collapsed state is inserted into lumen 33 of aspiration catheter 30 and advanced within lesion 101. Balloon 15 of the guidewire is inflated, either before or after introduction of the aspiration catheter and stent deployment catheter, to occlude the lumen of vessel 100, thereby protecting emboli from traveling downstream to other organs when stent 55 is expanded against lesion 101 by operating the actuating mechanism. After lumenal patency is re-established by deployment of the stent, fluid is infused through infusion lumens 36 and ports 35 to irrigate the vascular lumen within stent 55 while the distal end of catheter 50 remains within the stent as shown in FIG. 9A. Lumens 38 are attached to suction, and fluid, blood, and debris are aspirated into lumen 38 and removed.

Alternatively, the distal end of catheter 50 is withdrawn into lumen 33 of aspiration catheter 30 prior to irrigation and aspiration as shown in FIG. 9B. Removal of embolic debris is complete when the color of the aspirate turns from red to clear and the aspirate is free of any debris. After stent placement, balloon 15 on the guidewire is deflated to re-establish vascular flow, and the catheter system is removed from the vessel.

Figure 10:
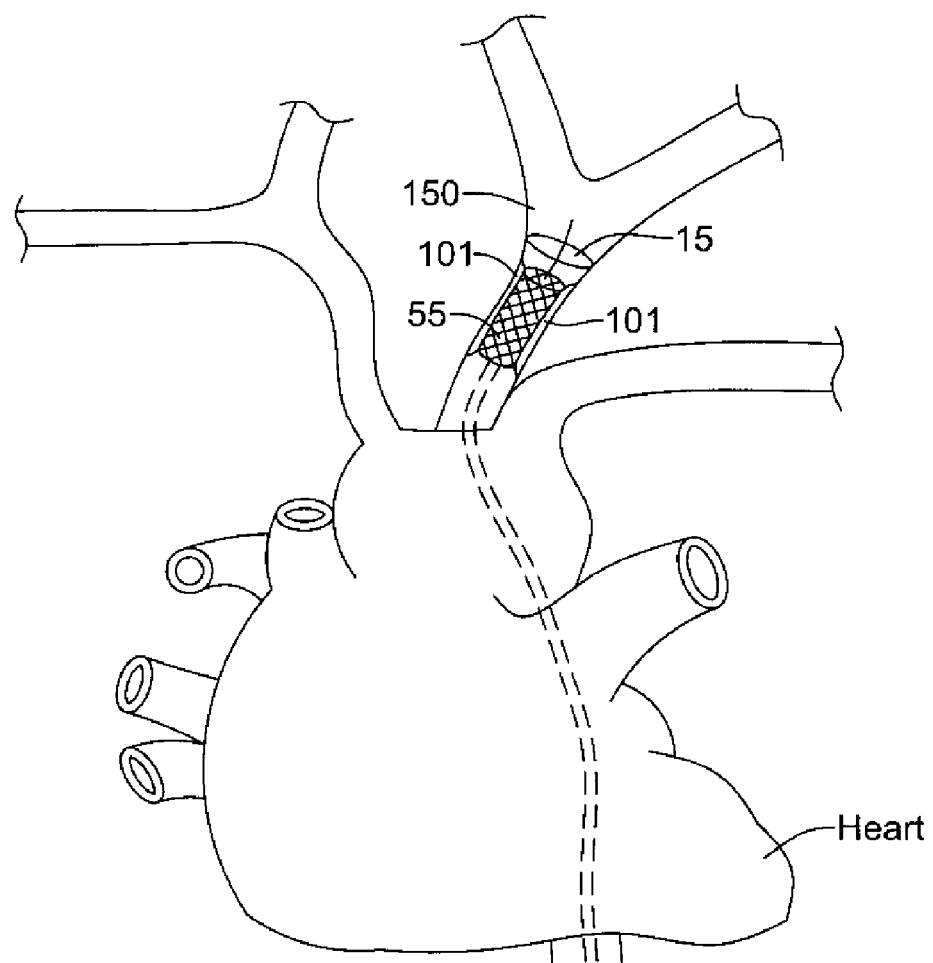
FIG. 10 depicts the catheter system of FIG. 8 inserted into the left common carotid artery for treatment of carotid stenosis.

FIG. 10 depicts the catheter system of FIG. 8 inserted into left common carotid artery 150 for treatment of carotid stenosis. The catheter system is inserted through an incision in left femoral artery 160 and advanced into the left common carotid artery via descending aorta 155. Stent 55 is deployed within lesion 101 while balloon occluder 15 of guidewire 10 is expanded to prevent distal embolization to the brain. Embolic material generated during carotid stenting is removed by irrigation and aspiration through catheter 30, thereby reducing the risk of cerebral ischemia and/or infarct.

FIG. 11 depicts another embodiment of the catheter system for treatment of a vascular lesion. Expandable balloon occluder 15 is mounted on distal end 71 of support wire 70, which is insertable through the lumen of angioplasty catheter 20.

In use, prior to inserting support wire 70 into a vessel, balloon occluder 15 is placed in a collapsed state by closing inflation valve 19 as depicted in FIGS. 12B and 12D. An endoluminal device, such as angioplasty catheter 20 having angioplasty balloon 25 mounted on a distal end, is inserted over support wire 70, and within aspiration catheter 30. After distal end 71 of the support wire is positioned downstream the region of interest, balloon occluder 15 is expanded by opening inflation valve 19 and infusing fluid or air through inflation lumen 16 as depicted in FIGS. 12A and 12C. Fluid, such as saline or Ringer's lactate, is infused through lumen 77 and port 75 to irrigate within the region of interest. Embolic debris, blood, fluid, and air are aspirated through either or both of lumen 76 of angioplasty catheter 20 and lumen 33 of aspiration catheter 30.

The length of the aspiration catheter will generally be between approximately 40 and 120 centimeters, preferably between approximately 60 and 80 centimeters. The length of the guidewire will generally be between approximately 50 and 130 centimeters, preferably between approximately 70 to 100 centimeters. The inner diameter of the aspiration catheter will generally be between approximately 0.5 and 2.0 centimeters, preferably approximately 0.8 and 1.5 centimeters for use in the aorta. The inner diameter of the guidewire will generally be between approximately 0.005 and 0.02 inches, preferably approximately 0.008 and 0.014 inches. The diameter of the expanded occluder on the guidewire will generally be between 2 and 6 centimeters, preferably approximately 3 and 5 centimeters for use in the aorta. For use in the carotid arteries, the inner diameter of the aspiration catheter will generally be between approximately 0.2 and 1.5 centimeters, preferably approximately 0.5 and 1.0 centimeters, and the diameter of the expanded occluder on the guidewire will generally be between 1 and 3 centimeters, preferably approximately 1.5 and 2.5 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claim. It will also be understood that each feature of each embodiment discussed herein, and of each reference cited herein, can be used in combination with the features of any other embodiment.

What is claimed is:

1. A system for endoluminal aspiration of embolic material, the system having a proximal end, a distal end and a longitudinal axis extending therebetween, the system comprising:

a guidewire having a proximal end and a distal end; and an aspiration catheter system having a proximal end and a distal end and having an aspiration lumen in fluid communication with a source of suction, an infusion lumen in fluid communication with a source of infusion fluid, a guidewire lumen adapted to receive the guidewire, wherein the aspiration lumen has a distal end and a first port at the aspiration lumen distal end, and wherein the infusion lumen has a distal end and a first port proximate the infusion lumen distal end, wherein the infusion lumen distal port faces generally radially with respect to the longitudinal axis, wherein the aspiration lumen distal port is distal the infusion lumen distal port, and wherein there are no intervening ports between the aspiration lumen distal port and the infusion lumen distal port, wherein the aspiration lumen and the infusion lumen are non-coaxial, and wherein the aspiration lumen distal port is an aspiration port at the aspiration catheter system distal end.

2. The system of claim 1, wherein the guidewire further comprises an expandable member disposed on the guidewire distal end.

3. The system of claim 2, wherein the expandable member is an occlusive member.

4. The system of claim 1, wherein the aspiration lumen distal port and infusion lumen distal port cooperate to create a venturi effect when the source of suction and the source of infusion fluid are operated.

5. The system of claim 1, wherein the aspiration lumen has a greater cross-sectional area at the distal end of the aspiration lumen than a cross-sectional area of the aspiration lumen at the distal end of the infusion lumen.

6. The system of claim 1, wherein the guidewire lumen extends distally of the aspiration and infusion lumens.

7. The system of claim 1, wherein the aspiration lumen distal port. faces distally.

8. The system of claim 1, wherein the aspiration lumen has a proximal end and wherein the aspiration lumen is defined by a wall of the aspiration catheter system having no openings between the aspiration lumen proximal end and the aspiration lumen distal port.

* * * * *